US008715624B2

(12) United States Patent
Rao et al.

(10) Patent No.: US 8,715,624 B2
(45) Date of Patent: *May 6, 2014

(54) STABLE LIQUID DESOXIMETHASONE COMPOSITIONS WITH REDUCED OXIDIZED IMPURITY

(75) Inventors: Srinivasa Rao, Valley Stream, NY (US); Suresh Dixit, Ft. Worth, TX (US); Avraham Yacobi, Englewood, NJ (US); Arthur Bailey, Bethel, CT (US)

(73) Assignee: Taro Pharmaceuticals North America, Inc., Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 13/605,622

(22) Filed: Sep. 6, 2012

(65) Prior Publication Data
US 2012/0328531 A1    Dec. 27, 2012

Related U.S. Application Data

(63) Continuation of application No. 11/921,106, filed as application No. PCT/US2006/020561 on May 26, 2006, now Pat. No. 8,277,780.

(60) Provisional application No. 60/685,676, filed on May 27, 2005.

(51) Int. Cl.
| A61K 9/08 | (2006.01) |
| A61K 31/573 | (2006.01) |
| A61K 9/12 | (2006.01) |
| A61K 9/14 | (2006.01) |

(52) U.S. Cl.
USPC ............... 424/45; 424/401; 424/46; 514/786; 514/863; 514/945

(58) Field of Classification Search
CPC ..... A61K 31/573; A61K 9/0078; A61K 9/12; A61K 9/0014; A61K 47/00; A61K 47/06; A61K 47/10; A61K 47/12; A61K 47/14; A61K 2300/00
See application file for complete search history.

(56) References Cited

U.S. PATENT DOCUMENTS

| 2,597,281 A | 5/1952 | Borstelmann et al. |
| 4,376,767 A | 3/1983 | Sloan |

(Continued)

FOREIGN PATENT DOCUMENTS

| JP | 06-256218 A | 9/1994 |
| WO | WO-85/01876 A1 | 5/1985 |
| WO | WO-99/33471 A1 | 7/1999 |

OTHER PUBLICATIONS

Derwent World Patent Information, vol. 41, No. 94, p. 13, 1994.

(Continued)

*Primary Examiner* — Lakshmi Channavajjala
(74) *Attorney, Agent, or Firm* — Venable LLP; Michael A. Gollin; Daniel A. Kopp

(57) ABSTRACT

The present invention relates to a stable liquid formulation comprising desoximetasone, isopropyl myristate, a $C_2$-$C_4$ alcohol and a stabilizing agent. Specifically, the present invention provides a liquid formulation comprising: a) about 0.01 wt % to about 2.5 wt % desoximetasone; b) about 10 wt % to about 70 wt % isopropyl myristate; c) about 20 wt % to about 70 wt % $C_2$-$C_4$ alcohol; and d) a stabilizing agent selected from the group consisting of an oleaginous vehicle and a propellant, wherein the stabilizing agent is in an amount sufficient to reduce the formation of less than about 1 wt % 17-carboxy-9α-fluoro-11β-hydroxy-16α-methyl-androsta-1,4-diene-3-one under an accelerated storage condition.

33 Claims, 10 Drawing Sheets

(56) References Cited

U.S. PATENT DOCUMENTS

Figure 1:
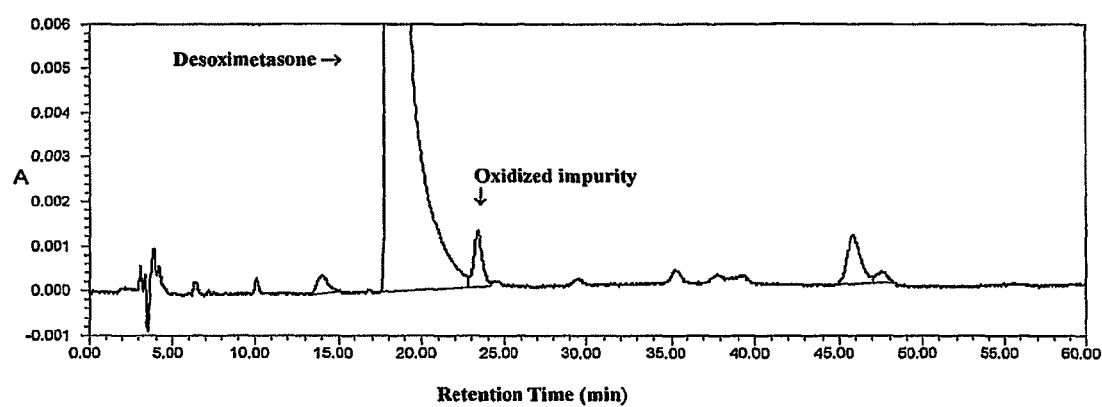

| | | | |
|---|---|---|---|
| 4,478,818 A | 10/1984 | Shell et al. | |
| 4,775,529 A | 10/1988 | Sequeira et al. | |
| 4,783,444 A | 11/1988 | Watkins et al. | |
| 4,840,772 A | 6/1989 | Watkins et al. | |
| 4,885,293 A | 12/1989 | Andrews et al. | |
| 4,970,206 A | 11/1990 | Alexander et al. | |
| 5,017,567 A | 5/1991 | Neustadt et al. | |
| 5,036,048 A | 7/1991 | Watkins | |
| 5,183,815 A | 2/1993 | Saari et al. | |
| 5,310,545 A | 5/1994 | Eisen | |
| 5,387,583 A | 2/1995 | Loria | |
| 5,407,663 A | 4/1995 | Eisen | |
| 5,543,417 A | 8/1996 | Waldstreicher | |
| 5,656,286 A | 8/1997 | Miranda et al. | |
| 5,776,433 A | 7/1998 | Tzou et al. | |
| 5,837,713 A | 11/1998 | Gleich | |
| 5,874,074 A | 2/1999 | Smith | |
| 5,962,010 A | 10/1999 | Greff et al. | |
| 5,972,920 A | 10/1999 | Seidel | |
| 5,990,100 A | 11/1999 | Rosenberg et al. | |
| 6,126,920 A | 10/2000 | Jones et al. | |
| 6,241,969 B1 | 6/2001 | Saidi et al. | |
| 6,315,985 B1 | 11/2001 | Wu et al. | |
| 6,335,023 B1 | 1/2002 | Yu et al. | |
| 6,352,686 B2 | 3/2002 | Bohn et al. | |
| 6,479,058 B1 | 11/2002 | McCadden | |
| 6,610,273 B2 | 8/2003 | Wu et al. | |
| 6,656,928 B1 | 12/2003 | McCadden | |
| 6,696,592 B2 | 2/2004 | McIntyre | |
| 6,740,327 B2 | 5/2004 | Yu et al. | |
| 6,824,786 B2 | 11/2004 | Yu et al. | |
| 6,830,758 B2 | 12/2004 | Nichols et al. | |
| 6,897,253 B2 | 5/2005 | Schmucker-Castner et al. | |
| 8,277,780 B2 * | 10/2012 | Rao et al. | 424/45 |
| 2004/0033201 A1 | 2/2004 | Wu et al. | |
| 2005/0232869 A1 | 10/2005 | Tamarkin et al. | |

OTHER PUBLICATIONS

ICH Guidance for Industry Q3B® Impurities in New Drug Products, Nov. 2003.
International Search Report dated Nov. 22, 2006, issued in Application No. PCT/US06/20561.
Office Action Issued by the U.S. Patent and Trademark Office for U.S. Appl. No. 11/921,106 on Dec. 30, 2011.
Office Action Issued by the U.S. Patent and Trademark Office for U.S. Appl. No. 11/921,106 on Jun. 6, 2011.
Office Action Issued by the U.S. Patent and Trademark Office for U.S. Appl. No. 11/921,106 on Sep. 21, 2010.
Sanders, P. "Aqueous Alcohol Aerosol Foams, Part I of a two-part Article," Drug and Cosmetic Industry, pp. 56-61, 142-143, 146-154, Aug. 1966.
Sanders, P. "Aqueous Alcohol Aerosol Foams, Second of a two-part article" Drug and Cosmetic Industry, pp. 57-58, 170-175, Sep. 1966.
Stoughton, R.B., The Same Glucocorticoid in Brand-Name Products. Arch. Dematol., vol. 125, pp. 1509-1511, 1989.
Supplementary European Search Report issued in EP Application No. 06771370 on Jun. 4, 2012.
Topicort Data Sheet. Revised Nov. 2004.

* cited by examiner

US 8,715,624 B2

STABLE LIQUID DESOXIMETHASONE COMPOSITIONS WITH REDUCED OXIDIZED IMPURITY

CROSS REFERENCE TO RELATED APPLICATIONS

This application is a Continuation of U.S. application Ser. No. 11/921,106, filed on Nov. 27, 2007, which is a U.S. National Stage of International Application No. PCT/US2006/020561, filed on May 26, 2006, which claims the benefit under 35 U.S.C. §119(e) of the U.S. Provisional Application No. 60/685,676 filed May 27, 2005. Each of these applications is incorporated by reference in its entirety and for all purposes.

FIELD OF THE INVENTION

The present invention relates to a stable liquid formulation comprising desoximetasone, isopropyl myristate, a $C_2$-$C_4$ alcohol and a stabilizing agent. The present liquid formulation is characterized by enhanced stability and reduced oxidized impurity (17-carboxy-9α-fluoro-11β-hydroxy-16α-methyl-androsta-1,4-diene-3 -one). The present invention also relates to a process for preparing a stable liquid formulation and a method of treating skin conditions including psoriasis.

BACKGROUND OF THE INVENTION

Chronic inflammatory disease such as psoriasis is a prevalent skin disease characterized by circumscribed red patches covered with white scales. The symptoms ranges from minimal lesions of the elbows and knees to a large number of lesions scattered over the skin. Current therapy of psoriasis includes topical administration of corticosteroid with the dosage forms of cream, ointment, and lotion.

U.S. Pat. No. 5,990,100 (the '100 patent) discloses isopropyl myristate as an active agent for treating psoriasis. The '100 patent further discloses the combined use of isopropyl myristate and an anti-psoriatic agent to form a more effective composition in treating psoriasis than either agent alone. Specifically, example 1 of the '100 patent discloses a formulation containing 40 wt % isopropyl myristate, 0.1 wt % sodium lauryl sulfate, 1.5 wt % polysorbate 80, 3.4 wt % water and 55 wt % ethanol. According to the '100 patent, topical application of the aerosolized formulation containing isopropyl myristate followed by topical application of calcipotriol ointment, desonide ointment or fluocinolone acetonide powder are more effective in treating psoriasis than either agent by itself.

U.S. Pat. No. 5,776,433 (the '433 patent) discloses an aerosolized flunisolide formulation useful in the treatment of inflammation of the nasal mucosa. In the '433 patent, hydrofluorocarbons is used as the propellant in a metered dose aerosol system containing a microcrystalline suspension of a steroid (i.e., flunisolide hemihydrate), propylene glycol, polyethylene glycol 3350, citric acid, sodium citrate, butylated hydroxyanisole, edetate disodium, benzalkonium chloride, and purified water. The '433 patent discloses that ethanol functions to solubilize the flunisolide, and the presence of water enhances to stabilize flunisolide. The '433 patent suggests the use of propellant to propel a plurality of flunisolide doses. While the '433 patent suggests the use of glass aerosol vial or aluminum aerosol vial having an interior chamber coated with an inert resin, it remains silent as to the agent(s) that may affect flunisolide stability.

U.S. Pat. No. 6,610,273 (the '273 patent) and U.S. Pat. No. 6,315,985 (the '985 patent) disclose that 20-ketosteroids rapidly begin to degrade when come in direct contact with aluminum oxide ($Al_2O_3$). 20-ketosteroids reaches a high degree of degradation (100% degradation) after addition of $Al_2O_3$ to an aerosolized formulation containing 20-ketosteroids. The '273 patent and '985 patent suggest the use of epoxy-phenolic lacquer or glass as an inert surface to minimize the degradation. Notably, the '985 patent states "the use of certain anti-oxidants such as ascorbic acid and ascorbyl palmitate (but not vitamin E) appeared to enhance chemical stability, while the use of oleic acid appeared to reduce chemical stability." (See, the '985 patent, col. 12, lines 2-5). Thus, the '985 patent suggests that the 20-ketosteroid degradation in the presence $Al_2O_3$ is inhibitable by anti-oxidants.

We surprisingly discovered that a liquid formulation comprising isopropyl myristate and desoximetasone suffers from oxidation of desoximetasone. The liquid formulation, even when stored with an inert surface (e.g., glass or canister) begins to deteriorate (i.e., formation of an oxidized impurity) when subjected to accelerated storage conditions (e.g., 40° C., 75% relative humidity for 3 months), indicating unsuitability of the product. Although present in small amounts, the level of oxidized impurity (after long-term storage) exceeds the qualification threshold and identification threshold calculated based on the maximum daily dosage. (See, ICH Guidance for Industry Q3B® Impurities in New Drug Products, November, 2003).

There is a continuing need for developing an aerosolized formulation of desoximetasone and isopropyl myristate that contains minimum acceptable levels of oxidized impurity. Prior art endeavors in this field have fallen short because no stable aerosolized formulations comprising desoximetasone and isopropyl myristate have been identified. The present invention meets this need by providing the use of a stabilizing agent in an aerosolized formulation suitable for long-term storage.

SUMMARY OF THE INVENTION

It is an object of the present invention to provide a stable liquid formulation of desoximetasone and isopropyl myristate that contains less than about 1 wt % oxidized impurity.

In one aspect, the present invention provides a liquid formulation comprising:
 a) about 0.01 wt % to about 2.5 wt % desoximetasone;
 b) about 10 wt % to about 70 wt % isopropyl myristate;
 c) about 20 wt % to about 70 wt % $C_2$-$C_4$ alcohol; and
 d) a stabilizing agent selected from the group consisting of an oleaginous vehicle and a propellant,.
 wherein the stabilizing agent is present in a sufficient amount to reduce the formation of less than about 1 wt % 17-carboxy-9α-fluoro-11β-hydroxy-16α-methyl-androsta-1,4-diene-3-one after storage at 40° C., 75% relative humidity for 3 months.

Preferably, the $C_2$-$C_4$ alcohol is either linear or branch. Preferably, the $C_2$-$C_4$ alcohol is ethyl alcohol. Preferably, the $C_2$-$C_4$ alcohol is isopropanol.

Preferably, oleaginous vehicle is selected from the group consisting of mineral oil, and light mineral oil. More preferably, the oleaginous vehicle is mineral oil.

Optionally, the stabilizing vehicle is a mixture of an oleaginous vehicle and a skin conditioning agent.

Preferably, the skin conditioning agent is an ester of glycerin and $C_{15}$-$C_{25}$ fatty acid. Preferably, the ester is a monoester. More preferably, the $C_{15}$-$C_{25}$ fatty acid is oleic acid. More preferably, the skin conditioning agent is glyceryl oleate.

Preferably, the skin conditioning agent is a $C_{15}$-$C_{25}$ fatty alcohol. More preferably, the $C_{15}$-$C_{25}$ fatty alcohol selected from the group consisting of lauryl alcohol, myristyl alcohol, palmityl alcohol, stearyl alcohol, linoleyl alcohol, and oleyl alcohol. More preferably, the $C_{15}$-$C_{25}$ fatty alcohol is oleyl alcohol.

Preferably, the propellant is selected from the group consisting of 1,1,1,2-tetrafluoroethane, 1,1,1,2,3,3,3-heptafluoropropane, butane, isobutane, propane, and dimethyl ether.

Preferably, the stable aerosolized formulation of desoximetasone and isopropyl myristate further comprises a surfactant.

Preferably, the surfactant selected from the group consisting of sodium lauryl sulfate, and polysorbate 80.

Preferably, the surfactant is present in the amount of about 0.5 wt % to about 5 wt %.

Preferably, the stable aerosolized formulation of desoximetasone and isopropyl myristate further comprises water.

Preferably, the water is present in the amount of about 1 wt % to about 10 wt %.

Preferably, the accelerated storage condition is 40° C., 75% relative humidity for a time period of 3 months. More preferably, the accelerated storage condition is 50° C. for a time period of 1 month.

Preferably, the stable aerosolized formulation of desoximetasone and isopropyl myristate is delivered via a pump delivery system. More preferably, the liquid formulation is delivered via an aerosolized delivery system.

Preferably, the aerosolized delivery system contains a can equipped with a continuous valve.

Preferably, the present liquid formulation may be in a foam dosage form.

Preferably, the present liquid formulation may be in a lotion dosage form.

In another aspect, the present invention provides a method of treating a corticosteroid responsive dermatosis comprising the step of topical administering the stable liquid formulation of desoximetasone and isopropyl myristate.

Preferably, the corticosteroid responsive dermatosis is selected from the group consisting of plaque psoriasis, and atopic dermatitis.

In another aspect, the present invention provides a process for preparing a stable liquid formulation of desoximetasone and isopropyl myristate comprising:

a) mixing desoximetasone in ethyl alcohol to from a mixture;
b) adding isopropyl myristate in the mixture; and
c) adding stabilizing agent to the mixture in an amount sufficient to reduce the formation of less than about 1 wt % oxidized impurity (17-carboxy-9α-fluoro-11β-hydroxy-16α-methyl-androsta-1,4-diene-3-one) under an accelerated storage condition.

In yet another aspect, the present invention provides a process for preparing a stable aerosolized formulation of desoximetasone and isopropyl myristate comprising the step of filling an aerosol formulation into a container equipped with a continuous valve, said aerosol formulation contains:

a) about 0.01 wt % to about 2.5 wt % desoximetasone;
b) about 10 wt % to about 70 wt % isopropyl myristate;
c) about 20 wt % to about 70 wt % $C_2$-$C_4$ alcohol; and
d) a stabilizing agent selected from the group consisting of a mixture of mineral oil and glyceryl oleate, a mixture of mineral oil and oleyl alcohol, and a propellant in an amount sufficient to reduce the formation of less than about 1 wt % oxidized impurity 17-carboxy-9α-fluoro-11β-hydroxy-16α-methyl-androsta-1,4-diene-3-one under an accelerated storage condition.

BRIEF DESCRIPTION OF THE DRAWINGS

FIG. 1 depicts the entire HPLC chromatogram summarizing the impurity profile for formulation no. 1 at time zero.

FIG. 2 depicts the entire HPLC chromatogram summarizing the impurity profile for formulation no. 1 after storage at 40° C./75% relative humidity for 12 weeks.

FIG. 3 depicts the entire HPLC chromatogram summarizing the impurity profile for formulation no. 5 (containing anti-oxidant of citric acid and tartaric acid) at time zero.

FIG. 4 depicts the entire HPLC chromatogram summarizing the impurity profile for formulation no. 5 (containing anti-oxidant of citric acid and tartaric acid) after storage at 50° C. for 4 weeks.

FIG. 5 depicts the entire HPLC chromatogram summarizing the impurity profile for formulation no. 7 (containing a stabilizing agent of a mixture of mineral oil and oleyl alcohol) at time zero.

FIG. 6 depicts the entire HPLC chromatogram summarizing the impurity profile for formulation no. 7 (containing a stabilizing agent of a mixture of mineral oil and oleyl alcohol) after storage at 40° C./75% relative humidity for 12 weeks.

FIG. 7 depicts the entire HPLC chromatogram summarizing the impurity profile for formulation no. 11 (containing a stabilizing agent of a mixture of mineral oil and glyceryl oleate) at time zero.

FIG. 8 depicts the entire HPLC chromatogram summarizing the impurity profile for formulation no. 11 (containing a stabilizing agent of a mixture of mineral oil and glyceryl oleate) after storage at 40° C./75% relative humidity for 12 weeks.

FIG. 9 depicts the entire HPLC chromatogram summarizing the impurity profile for formulation no. 12 (containing a stabilizing agent of a propellant) at time zero.

FIG. 10 depicts the entire HPLC chromatogram summarizing the impurity profile for formulation no. 11 (containing a stabilizing agent of a propellant) after storage at 40° C./75% relative humidity for 12 weeks.

DETAILED DESCRIPTION OF THE INVENTION

Definitions:

As used herein, the definition of terms are listed as follow:

"stabilizing agent" refers to an agent that improves stability of the liquid formulation and prevent the formation of oxidized impurity (17-carboxy-9α-fluoro-11β-hydroxy-16α-methyl-androsta-1,4-diene-3 -one);

"oleaginous vehicle" refers to a solvent that resembles or having the properties of oil such as vegetable oil (corn, cottonseed, olive, peanut and sesame seed oils) or mineral oil;

"propellant" refers to a compound effective in dispensing the active ingredients into a fine mist or foam;

"mineral oil" refers to a mixture of refined liquid saturated hydrocarbons obtained from petroleum. Viscosity (at 40° C.) and specific gravity of mineral oil usually is ≥34.5 cSt and between 0.845-0.905, respectively. CAS registry no. is 8012-95-1;

"light mineral oil" refers to a mixture of refined liquid saturated hydrocarbons obtained from petroleum. It is less viscous and has lower specific gravity than mineral oil. Viscosity (at 40° C.) and specific gravity of light mineral oil usually is ≤33.5 cSt and between 0.818-0.880, respectively;

"glycerin" refers to a polyhydric alcohol that conforms generally to the formula: $HOCH_2CH(OH)CH_2OH$;

"oleyl alcohol" refers to the unsaturated fatty alcohol that conforms generally to the formula: $CH_3(CH_2)_7CH=CH(CH_2)_8OH$;

"skin conditioning agent"—for purposes of the present invention, "skin conditioning agent" encompasses ,a monoester of a glycerin and a $C_{15}$-$C_{25}$ fatty acid and a $C_{15}$-$C_{25}$ fatty alcohol;

"fatty alcohol" refers aliphatic alcohol that occurs naturally in free form (component of the cuticular lipids) but more usually in esterified (wax esters) or etherified form (glyceryl ethers);

"ester" refers to any one of a group of organic compounds with general formula $RCO_2R'$ (where R and R' are alkyl groups or aryl groups) that are formed by the reaction between an alcohol and an acid;

"monoester" refers to an ester having only one ester group;

"oxidized impurity"—for purposes of the present invention, "oxidized impurity" identified in the present formulation having a relative retention time of 1.26, a retention time usually between 20 and 30 minutes, and physical chemical properties as detailed in the "Example section" refers to 17-carboxy-9α-fluoro-11β-hydroxy-16β-methyl-androsta-1,4-diene-3-one;

"aerosol" refers to the products which depends upon the power of a liquefied or compressed gas to disperse the active ingredients in a finely dispersed mist, foam or semisolid. For purpose of the present invention, pump systems which also dispense the active ingredients in the form of a finely dispersed mist (although of greater particle size) are intended to be encompassed as aerosol;

"accelerated storage condition" refers to storage of a liquid formulation under the conditions of either 40° C., 75% relative humidity for 12 weeks or 50° C. for 4 weeks. These storage conditions are equivalent to that of 25°-30° C., 60% relative humidity for twenty-four (24) months (i.e., long-term storage).

"topical administration" refers to local administration to the skin of the liquid or semi-solid formulation and its various embodiments;

"mammal" refers to a class of higher vertebrates comprising man and all other animals that nourish their young with milk secreted by mammary glands and have the skin usually more or less covered with hair; and "treating" is intended to encompass relieving, alleviating or eliminating at least one symptom of a dry skin diseases in a mammal.

Unless otherwise specified, % refers to % wt; and % wt refers to % of weight of respective component with respect to the total weight of the composition.

Inventors of the present invention unexpectedly discovered a stable liquid formulation comprising desoximetasone, isopropyl myristate, $C_2$-$C_4$ alcohol and a stabilizing agent and a method for treating a patient for a skin condition, comprising the step of administering such a stable liquid formulation. The present formulation and method offer significant advantages over the prior art in that it provides enhanced stability of the liquid formulation that is useful in treating the skin conditions.

While the use of epoxy-phenolic lacquer or glass as an inert surface is suggested to reduce the degradation of 20-ketosteroids (See, U.S. Pat. No. 6,610,273), inventors of the present invention found that there is still a significant formation of oxidized impurity in a liquid formulation comprising desoximetasone, isopropyl myristate and $C_2$-$C_4$ alcohol. Inventors of the present invention characterized and identified the oxidized impurity as 17-carboxy-9α-fluoro-11β-hydroxy-16α-methyl-androsta-1,4-diene-3-one. The formation of the oxidized impurity occurs upon accelerated storage conditions, even when the liquid formulation is stored (i.e., in direct contact with) in glass.

In its active pharmaceutical ingredient (API) form, desoximetasone has three (3) impurities; namely: i) impurity S, ii) 17-desoxiosido- and iii) 17-carboxy-9α-fluoro-11β-hydroxy-16α-methyl-androsta-1,4-diene-3-one. Of these 3 impurities, only the 17-carboxy-9α-fluoro-11β-hydroxy-16α-methyl-androsta-1,4-diene-3-one was found to increase in the liquid formulation upon accelerated storage conditions. This finding indicates that this particular impurity of 17-carboxy-9α-fluoro-11β-hydroxy-16α-methyl-androsta-1,4-diene-3-one uniquely increases upon accelerated storage conditions with respect to a liquid formulation comprising desoximetasone, isopropyl myristate, $C_2$-$C_4$ alcohol.

Because the level of the oxidized impurity exceeds the qualification threshold and identification threshold calculated based on the maximum daily dosage, it renders the liquid formulation unsuitable for commercial use.

Inventors of the present invention unexpectedly discovered that the formation of 17-carboxy-9α-fluoro-11β-hydroxy-16α-methyl-androsta-1,4-diene-3 -one is different from degradation of 20-ketosteroids via its interaction of $Al_2O_3$. While the interaction of $Al_2O_3$ is completely blocked by anti-oxidants (See, U.S. Pat. No. 6,315,985), the formation of 17-carboxy-9α-fluoro-11β-hydroxy-16α-methyl-androsta-1,4-diene-3-one is not affected by addition of anti-oxidants at all (See, Table 5 of "Example" Section below). On the contrary, additional impurities were found to be generated (See, Table 6 of "Example" Section below).

Inventors of the present invention surprisingly discovered that addition of a stabilizing agent enhances the stability of the liquid formulation comprising desoximetasone, isopropyl myristate and a $C_2$-$C_4$ alcohol. Without wishing to be bound by a theory, it is believed that the stabilizing agent inhibits the formation of the oxidized impurity (17-carboxy-9α-fluoro-11β-hydroxy-16α-methyl-androsta-1,4-diene-3-one), probably via an oxidation pathway that is not sensitive to anti-oxidants. According to the present invention, the addition of a stabilizing agent therefore offers a much improved liquid formulation comprising desoximetasone, isopropyl myristate and a $C_2$-$C_4$ alcohol.

Accordingly, the present invention is directed to a stable liquid formulation containing a steroid (i.e., desoximetasone) in therapeutic amounts to alleviate the symptoms of dermatosis skin conditions. For the purposes of the present invention, desoximetasone encompasses the salt forms of desoximetasone as exemplified by desoximetasone hydrochloride or desoximetasone acetate.

The therapeutically amount of the desoximetasone in the present stable liquid formulation is generally within the range of from about 0.01 wt % to 2.5 wt % of the formulation. Preferably, the desoximetasone is present in the amount of about between about 0.1 wt % to about 1 wt %. More preferably, the desoximetasone is present in the amount of about 0.25 wt %.

Accordingly, the present invention provides a stable liquid formulation containing isopropyl myristate. Preferably, isopropyl myristate is present in the amount of about from about 10 wt % to about 70 wt %. More preferably, isopropyl myristate is present in the amount of about 25 wt % and 55 wt %. More preferably, isopropyl myristate is present in the amount of about 40 wt %.

Accordingly, the present invention also provides a stable liquid formulation containing a $C_2$-$C_4$ alcohol. The $C_2$-$C_4$ alcohol may encompass a linear or branch $C_2$-$C_4$ alcohol. Preferably, the $C_2$-$C_4$ alcohol is ethyl alcohol. Preferably, the $C_2$-$C_4$ alcohol is isopropanol.

Preferably, the $C_2$-$C4$ alcohol is present in the amount of from about 20 wt % to about 70 wt %. More preferably, the $C_2$-$C_4$ alcohol is present in the amount of from about 30 wt % to about 60 wt %. More preferably, the $C_2$-$C_4$ alcohol is present in the amount of about 40 wt %.

In one preferred embodiment, stabilizing agent used in the present invention is an oleaginous vehicle.

Preferably, oleaginous vehicle includes, but not limited to, mineral oil, and light mineral oil. Other suitable oleaginous vehicle includes apricot kernel oil, canola oil, castor oil, coconut oil, corn oil, cottonseed oil, olive oil, soybean oil or vegetable oil.

Preferably, oleaginous vehicle is present in the amount of about 10 wt % to to about 60 wt %. More preferably, oleaginous vehicle is present in the amount of about 20 wt % and 50 wt %. More preferably, oleaginous vehicle is present in the amount of about 40 wt %.

Optionally, the stabilizing agent is a mixture of an oleaginous vehicle and a skin conditioning agent. Such a mixture of an oleaginous vehicle and a skin conditioning agent would also found to be effective to prevent the formation of oxidized impurity when added into the liquid formulation.

In another preferred embodiment, skin conditioning agent is a ester of a glycerin and a $C_{15}$-$C_{25}$ fatty acid. Preferably, the ester is a monoester. Preferably, the $C_{15}$-$C_{25}$ fatty acid is oleic acid. Preferably, the ester is glyceryl oleate.

In another preferred embodiment, skin conditioning agent is a $C_{15}$-$C_{25}$ fatty alcohol. An unsaturated $C_{15}$-$C_{25}$ fatty alcohol includes, but not limited to, lauryl alcohol, myristyl alcohol, palmityl alcohol, stearyl alcohol, linoleyl alcohol, oleyl alcohol and the like. More preferably, the $C_{15}$-$C_{25}$ fatty alcohol is oleyl alcohol.

Preferably, skin conditioning agent is present in the amount of about 0.5 wt % to about 10 wt %. More preferably, skin conditioning agent is present in the amount of about 1 wt % and about 8 wt %. More preferably, skin conditioning agent is present in the amount of about 5 wt %.

Preferably, stabilizing agent used in the present invention is a mixture of mineral oil and oleyl alcohol.

Preferably, stabilizing agent used in the present invention is a mixture of mineral oil and glyceryl oleate.

Preferably, the mixture of an oleaginous vehicle and a skin conditioning agent is present in an amount sufficient to inhibit the formation of oxidized impurity after accelerated storage condition (e.g., 40° C./75% relative humidity for 12 weeks or 50° C. for 4 weeks).

In another preferred embodiment, stabilizing agent used in the present invention is propellant. Preferred propellant in the present stable formulation includes, but not limited to, 1,1,1,2-tetrafluoroethane, and 1,1,1,2,3,3,3-heptafluoropropane. Suitable propellant also includes butane, isobutane, propane, and dimethyl ether. More preferably, the propellant is 1,1,1,2-tetrafiuoroethane.

Preferably, propellant is present in an amount sufficient to inhibit the formation of oxidized impurity after accelerated storage condition (e.g., 40° C./75% relative humidity for 12 weeks). Preferably, propellant is present in about 20 wt % to about 95 wt %. More preferably, propellant is present in about 40 wt % to about 80 wt %. More preferably, propellant is present in about 75 wt %.

The stable liquid formulation may further comprise surfactant. Preferably, the surfactant includes, but not limited to sodium lauryl sulfate, and polysorbate 80.

Preferably, surfactant is present in the amount of about 0.5 wt % to about 5 wt %. More preferably, surfactant is present in the amount of about 1 wt % and about 3 wt %. More preferably, surfactant is in the amount of about 1 wt %.

The stable liquid formulation may further comprise water. Preferably, water is present in the amount of about 1 wt % to about 10 wt %. More preferably, water is present in the amount of about 2 wt % and 6 wt %. More preferably, water is present in the amount of about 3 wt %.

Preferably, the accelerated storage condition is 40° C., 75% relative humidity for a time period of 3 months. Preferably, the accelerated storage condition is 50° C. for a time period of 1 month.

The present liquid formulation may be delivered via suitable delivery system. Preferably, the present liquid formulation is delivered via an aerosolized delivery system. Preferably, the present liquid formulation may be delivered via a pump delivery system. Preferably, the aerosolized delivery system contains a can equipped with a continuous valve. Preferably, the aerosolized delivery system contains a can equipped with a meter-dosed valve.

In another preferred embodiment, the present invention provides a foam pharmaceutical composition containing a corticosteroid (e.g., desoximetasone), isopropyl myristate, $C_2$-$C_4$ alcohol, an oleaginous vehicle as a stabilizing agent, and a foam-forming agent. Preparation of a foam pharmaceutical composition is known. Suitable foam-forming agents include, but not limited to, surfactants exemplified by cetyl alcohol, stearyl alcohol, ethoxylated stearyl alcohol, polawax, and the like. (See, e.g., Sanders P. "Aqueous Alcohol Aerosoal Foams"; D&CI/August 1966). One or more foam-forming agent(s) may be used. Proper concentration of foam-forming agents may easily be optimized by one skill in the art.

The present liquid formulation may also be formulated into a quick-break foam. When applied to skin, the foam composition is initially in the form of a mousse-like foam, but will slowly break down at the skin temperature to liquid. This would allow the desoximetasone and isopropyl myristate to saturate the treatment site.

Quick-break foaming agents that can be used in the present invention are generally known (See, e.g., WO 85/01876). It is preferred that the quick-breaking foaming agent comprises an aliphatic alcohol, water, a fatty alcohol and a surface-active agent.

In yet another preferred embodiment, the present invention provides a lotion pharmaceutical composition containing a corticosteroid (i.e., desoximetasone), isopropyl myristate, $C_2$-$C_4$ alcohol, a stabilizing agent (e.g., an oleaginous vehicle) in an isopropyl myristate base. Lotions may be liquid preparations. The present liquid formulation may be an emulsified or non-emulsified lotion. Preferably, the present liquid formulation is a non-emulsifying lotion. Optionally, the lotions may contain an antimicrobial preservative and other appropriate excipients such as a thickening agent (to increase viscosity).

The present invention provides a method of treating a corticosteroid responsive dermatosis comprising the step of topical administering the aerosolized formulation. The corticosteroid responsive dermatosis is selected from the group consisting of plaque psoriasis, and atopic dermatitis.

The present invention provides a method of preparing a stable liquid formulation. The preparation method is detailed hereinafter.

Method of Preparation

In one preferred embodiment, the present invention provides a method for preparing a stable liquid formulation, comprising the steps of:

a) combining desoximetasone, $C_2$-$C_4$ alcohol and isopropyl myristate to form a mixture;
b) optionally adding water, sodium lauryl sulfate, or polysorbate 80 into the mixture; and
c) adding a stabilizing agent into the mixture to form a stable liquid formulation.

Preferably, the stabilizing agent is selected from the group consisting of an oleaginous vehicle and a propellant. Preferably, the oleaginous vehicle is mineral oil or light mineral oil. Preferably, the stabilizing agent is a mixture of mineral oil and glyceryl oleate. Preferably, the stabilizing agent is a mixture of mineral oil and oleyl alcohol. Preferably, the stabilizing agent is a propellant. Preferably, the stabilizing agent is in an amount sufficient to reduce the formation of less than about 1 wt % oxidized impurity under an accelerated storage condition.

The present invention is directed to a method of treating skin conditions in a mammal. More particularly, the present invention provides a method of treating skin conditions in a patient by providing an improved stable liquid formulation comprising therapeutic effective amounts of desoximetasone and isopropyl myristate. According to the present invention, the term "patient" will encompass any mammal requiring treatment for skin conditions, particularly a human patient suffering from dermatosis.

For the purpose of the present invention, dermatosis condition includes, but are not limited to, all conditions of psorasis and atopic dermatitis.

The dosage for the desoximetasone and isopropyl myristate of the invention will vary depending on several factors, including, but not limited to, the age, weight, and species of the patient, the general health of the patient, the severity of the symptoms in dermatosis skin conditions.

Analytical Protocol:

Contents of desoximetasone and its related impurities (including the oxidized impurity) were determined by using the following High Performance Liquid Chromatography (HPLC) protocol. In this protocol, a HPLC instrument with a chromatograph and an ultra-violet detector was used. The HPLC condition was:

| Column | Waters Symmetry C18, 4.6 × 250 mm, 5 μm particle diameter |
|---|---|
| Flow Rate | 0.8 ml/min isocratic |
| Detection | UV at 275 nm |
| Injection Volume | 5 μL |
| Column Temperature | 25° C. |
| Mobile Phase | 360 grams of acetonitrile was dissolved in 600 grams of water to it 30 grams of methanol was added followed by 10 grams of acetic acid and mixed. |

Having now generally described this invention, the same will be better understood by reference to the following Examples, which are provided herein solely for purposes of illustration only and are not intended to be limiting of the invention or any embodiment thereof, unless so specified. All parts and percentages referred to in this specification and the appended claims are by weight unless otherwise specified.

EXAMPLES

Example 1

Impurities Present in Desoximetasone API

We analyzed the impurities present in the active pharmaceutical ingredient (API) dexosimetasone using HPLC technique. A total of not more than 1.0% impurities were found to be present in the dexosimetasone API. Of the total impurities found, three (3) main impurities were identified to be:

1) oxidized impurity (not more than 0.5%);
2) impurity S (not more than 0.5%); and
3) 17-desoxi-oxido intermediate or desoxi-oxido (not more than 0.5%).

The chemical structures of these three (3) main impurities were determined and are depicted as follows:

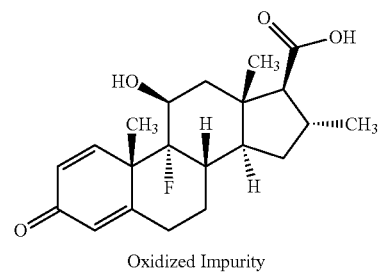

Oxidized Impurity 17-carboxy-9α-fluoro-11β-hydroxy-16α-methyl-androsta-1,4-diene-3-one (Oxidized Impurity)

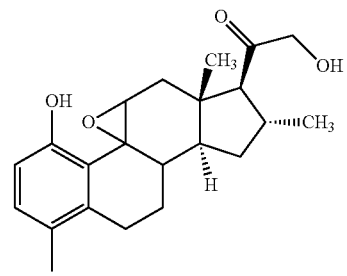

Impurity S

1-Hydroxy-4,16α-dimethyl-9β,11β-oxido-17 hydroxymethylcarbonylestra-1,3,5(10)triene (Impurity S)

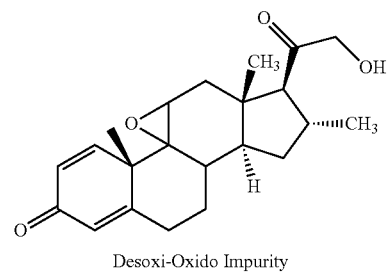 [SMILES: C[C@@H]1C[C@H]2C3CCC4=CC(=O)C=C[C@]4(C)C34OC4C[C@]2(C)[C@H]1C(=O)CO]

Desoxi-Oxido Impurity

21-Hydroxy-16α-methyl-9β,11β-oxido-pregna-1,4-diene-3.20-dione (17-desoxi-oxido intermediate or desoxi-oxido impurity)

Example 2

Control Formulation No. 1 Containing Desoximetasone and Isopropyl Myristate (Comparative Example)

Formulation: Control formulation no. 1 containing desoximetasone and isopropyl myristate was prepared with specified ingredients as tabulated in Table 1.

TABLE 1

| Ingredients | wt % |
| --- | --- |
| Active | |
| Desoximetasone | 0.25% |
| Penetration Enhancer | |
| Isopropyl Myristate | 40.0% |
| Solvent | |
| Purified Water | 3.40% |
| Ethyl Alcohol | 54.75% |
| Surfactant | |
| Sodium Lauryl Sulfate | 0.10% |
| Polysorbate 80 | 1.50% |

Preparation: The formulation was prepared as follows: desoximetasone (0.25 wt %) was first dissolved in ethyl alcohol (54.75 wt %) at room temperature (i.e., 25° C.). Isopropyl myristate (40.0 wt %) was then added to the mixture followed by addition of purified water (3.40 wt %), sodium lauryl sulfate (0.10 wt %), and polysorbate 80 (1.50 wt %). The resulting mixture was further stirred for 15 minutes at room temperature.

Stability Study: We conducted the stability of desoximetasone formulation no. 1. Formulation no. 1 containing desoximetasone and isopropyl myristate was placed in a 20-ml glass vial. Formulation no. 1 was then subjected under accelerated storage condition (i.e., 40° C., 75% humidity for 12 weeks). Contents of desoximetasone and the three (3) impurities described above (i.e., oxidized impurity, impurity S, and 17-desoxi-oxido intermediate) were evaluated using HPLC technique.

When formulation no. 1 was stored at 40° C., 75% humidity for 12 weeks, we surprisingly found that only one (1) of the three (3) impurities (i.e., oxidized impurity) was found to increase more than 10 fold. The level of impurity S and 17-desoxi-oxido intermediate, however, was found to be undetectable (i.e., below the limit of detection), both in the control and upon accelerated storage conditions.

The level of the oxidized impurity (i.e., 17-carboxy-9α-fluoro-11β-hydroxy-16α-methyl-androsta-1,4-diene-3-one) exceeded the qualification threshold and identification threshold calculated based on the maximum daily dosage. The data is tabulated in Table 2.

TABLE 2

| Content | 0 Week | 12 Weeks |
| --- | --- | --- |
| Desoximetasone (% Time Zero) | 100.0% | 96.24% |
| Oxidized Impurity (% Area) | 0.13% | 2.49% |

Characterization of the Oxidized Impurity

We have isolated the oxidized impurity (having a relative retention time of 1.26) from the HPLC. We conducted Elemental Analysis of the isolated oxidized impurity:
Calculated: C=67.92; H=7.54; F=5.12%
Found: C=68.20; H=7.41, F=5.47%
Conformed with the formula of a hemihydrate.

We analyzed the oxidized impurity using Infrared Spectroscopy. Infrared spectrum characteristic bands and assignments (KBr pellet):
3282 cm$^{-1}$ (broad, OH),
1730 cm$^{-1}$ (C=O),
1694 cm$^{-1}$ (C=O),
1661 cm$^{-1}$ (C=C),
1609 cm$^{-1}$ (C=C).

We analyzed the oxidized impurity using Ultra-Violet Spectroscopy. The UV maximum in methanol (1×10-4M/L) was determined to be at wavelength 239 nm, the molar absorbtivity c was 15,500.

We analyzed the oxidized impurity using NMR Spectroscopy (D2O+NaOD) to determine the structure. The $^1$H-NMR spectrum is (δ, ppm):7.32 (d, J=9.6, 1H, H-1), 6.19 (d, J=9.8, 1H, H-2), 5.95 (s, 1H, H-4), 4.02-4.07 (m, 1H, H-11), 2.69 (complex system of lines, 1H), 2.17-2.21 (complex system of lines, 3H), 1.30-1.81 complex system of lines, 7H), 1.39 (s, 3H, CH$_3$-19), 1.25-1.47 (m, 1H), 0.75 (d, 3H, CH$_3$-22), 0.74 (s, 3H, CH$_3$-18).

High Resolution Mass Spectrometry was conducted. The molecular ion at ink 363.1891 (MH+) was found to correspond to formula C$_{21}$H$_{27}$FO$_4$. This structural analysis confirmed the identity of the oxidized impurity as 17-carboxy-9α-fluoro,11β-hydroxy-16α-methylandrosta-1,4-diene-3-one. The melting point of the oxidized impurity was determined to be >250° C.

Profile of Other Impurities: In addition to the three (3) impurities (as described above), we also monitored other impurities that may be present in the formulation during the accelerated storage conditions. Table 3 depicts the complete impurity profile of the control formulation no.1 after storage at 40° C. and 75% humidity for 12 weeks. The main impurity was the oxidized impurity, which has an elution retention time (RT) of 22.596. The % area of the oxidized impurity was 2.49% area. There were six (6) minor impurities with different retention times. The total amount of these minor impurities was less than about 0.6% area. Based on their retention times, it is believed that they do not overlap with those of: 1) impurity S, and 2) 17-desoxi-oxido intermediate. The chemical identity of these six (6) minor impurities is presently unknown.

TABLE 3

| RT | Impurity | % Area |
| --- | --- | --- |
| 9.791 | Unknown | 0.09 |
| 13.030 | Unknown | 0.06 |
| 13.583 | Unknown | 0.04 |
| 22.596 | Oxidized Impurity | 2.49 |
| 37.687 | Unknown | 0.11 |
| 44.502 | Unknown | 0.08 |
| 45.737 | Unknown | 0.22 |

The entire HPLC chromatogram summarizing the impurity profile for formulation no. 1 at time zero is shown in FIG. 1.

Figure 2:
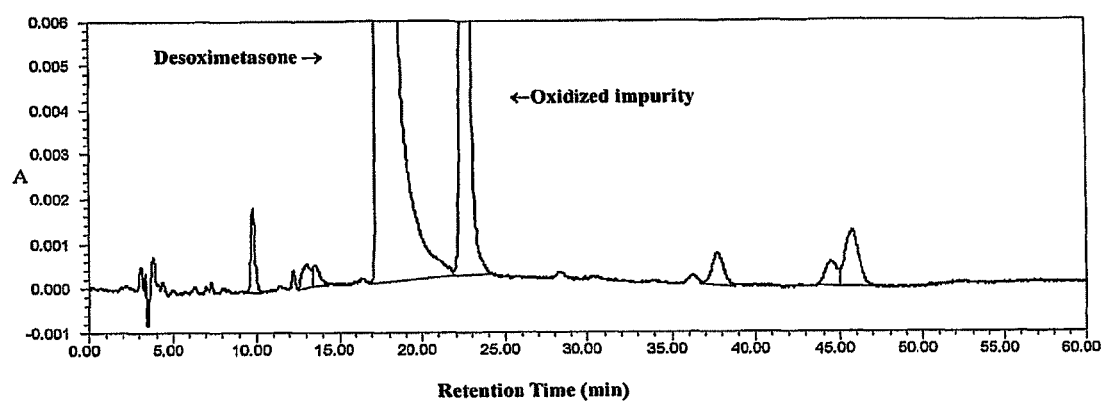

The entire HPLC chromatogram summarizing the impurity profile for formulation no. 1 after storage at 40° C./75% relative humidity for 12 weeks is shown in FIG. 2.

Example 2

Formulation Nos. 2-6 Containing Desoximetasone, Isopropyl Myristate and Various Anti-Oxidants Formulation: We evaluated if anti-oxidants may reduce the formation of impurities during the accelerated storage condition. Various anti-oxidants were added to the formulation nos. 2-6 containing desoximetasone and isopropyl myristate and impurity profiles were determined. Specifically, anti-oxidants butylated hydroxyanisole (BHA), butylated hydroxytoluene (BHT), ascorbic acid, tartaric acid and DL-alpha tocopherol in combination with citric acid were used at various concentrations as tabulated in Table 4.

TABLE 4

| Ingredients | Formul. No. 2 | Formul. No. 3 | Formul. No. 4 | Formul. No. 5 | Formul. No. 6 |
| --- | --- | --- | --- | --- | --- |
| Active | | | | | |
| Desoximetasone | 1.0% | 1.0% | 1.0% | 1.0% | 1.0% |
| Penetration Enhancer | | | | | |
| Isopropyl Myristate | 40.0% | 40.0% | 40.0% | 40.0% | 40.0% |
| Solvent | | | | | |
| Purified Water | 1.10% | 0.90% | 1.35% | 1.3% | 1.40% |
| Ethyl Alcohol | 57.10% | 57.10% | 57.10% | 57.10% | 57.10% |
| Surfactant | | | | | |
| SLS | 0.10% | 0.10% | 0.10% | 0.10% | 0.10% |
| Polysorbate 80 | 0.15% | 0.15% | 0.15% | 0.15% | 0.15% |
| Antioxidants | | | | | |
| Citric Acid | 0.25% | 0.25% | 0.25% | 0.25% | 0.25% |
| BHA | 0.10% | — | — | — | — |
| BHT | 0.20% | 0.50% | — | — | — |
| Ascorbic Acid | — | — | 0.05% | — | — |
| Tartaric Acid | — | — | — | 0.10% | — |
| DL-alpha Tocopherol | — | — | — | — | 0.002% |

Preparation: The formulation was prepared as follows: desoximetasone (1.0 wt %) was dissolved in ethyl alcohol (57.10 wt %) at room temperature (i.e., 25° C.). Isopropyl myristate (40.0 wt %) was added to the mixture followed by purified water, sodium lauryl sulfate (0.10 wt %), and polysorbate 80 (0.15 wt %). Antioxidants were added and mixed in accordance to the specific formulation. The resulting mixtures were further stirred for 15 minutes at room temperature.

Stability Study: We conducted the stability of formulation nos. 2-6 by subjecting the formulations under accelerated storage condition (i.e., 50° C. at for 4 weeks). Formulation no. 2-6 containing desoximetasone and isopropyl myristate was placed in a 20-ml glass vial stored at 50° C. for 4 weeks.

Content of desoximetasone and impurities were evaluated using HPLC technique. The data is tabulated in Table 5.

TABLE 5

| Content | Time points | Formul. No. 2 | Formul. No. 3 | Formul. No. 4 | Formul. No. 5 | Formul. No. 6 |
| --- | --- | --- | --- | --- | --- | --- |
| Desoximetasone (% Time Zero) | 0 week | 100.0% | 100.0% | 100.0% | 100.0% | 100.0% |
| | 2 weeks | 95.60% | 96.10% | 96.80% | 96.70% | 98.90% |
| | 4 weeks | 90.40% | 88.30% | 95.50% | 92.30% | 93.90% |
| Oxidized Impurity (% Area) | 0 week | 0.13% | 0.14% | 0.13% | 0.13% | 0.11% |
| | 2 weeks | 1.13% | 0.96% | 0.92% | 1.45% | 1.0% |
| | 4 weeks | 3.15% | 3.37% | 2.52% | 4.17% | 2.90% |

Impurity Profile: Table 6 depicts the impurity profile of the formulation nos. 2-6 after accelerated storage condition (i.e., 50° C. for 4 weeks). The main impurity present in the formulation nos. 2-6 was the oxidized impurity (17-carboxy-9α-fluoro-11β-hydroxy-16α-methyl-androsta-1,4-diene-3-one). Anti-oxidants simply did not inhibit the formation of the oxidized impurity in all the formulations tested (See, Table 5).

Not only anti-oxidants fail to inhibit the formation of oxidized impurity, it led to the generation of a lot more impurities. Specifically, a total of twelve (12) minor impurities were eluted from formulation no. 2, five (5) minor impurities were eluted from formulation no. 3, nine (9) minor impurities were eluted from formulation no 4 and six (6) minor impurities were eluted form formulation nos. 5 and 6.

It is found that these minor impurities do not share the retention time with that of i) the oxidized impurity, ii) impurity S and iii)17-desoxi-oxido intermediate. Accordingly, it is concluded that the chemical structure of these minor impurities are not the same as that of i) the oxidized impurity, ii) impurity S and iii)17-desoxi-oxido intermediate. However, the exact chemical structure of these minor impurities has not been determined and is presently unknown.

Of note is the observation that the oxidized impurity has a distinct retention time (i.e., about 21.994 to about 22.996) for formulation nos. 2-6, due to the intrinsic variations of the HPLC conditions. The maximum % area of the oxidized impurity was 4.17 (i.e., formulation no. 5). The minimum % area of the oxidized impurity was 2.52 (i.e., formulation no. 4). (See, Table 6).

The total % area of the minor impurities was less than about 4% area. The maximum % area of the minor impurities was 3.42 (i.e., formulation no. 2). The minimum % area of the minor impurities was 1.13 (i.e., formulation no. 5). (See, table 6).

TABLE 6

| Impurity Type | Formul. No. 2 | Formul. No. 3 | Formul. No. 4 | Formul. No. 5 | Formul. No. 6 |
| --- | --- | --- | --- | --- | --- |
| Oxidized Impurity | 3.15% (RT 22.976) | 3.37% (RT 22.639) | 2.52% (RT 22.453) | 4.17% (RT 22.392) | 2.90% (RT 21.994) |
| Unknown Impurity | 0.05% (RT 6.264) | — | 0.26% (RT 6.672) | — | — |
| | — | — | 0.04% (RT 8.946) | — | — |
| | 0.03% (RT 9.946) | — | 0.07% (RT 9.765) | 0.07% (RT 9.730) | 0.06% (RT 9.581) |
| | 0.09% | — | — | — | — |

TABLE 6-continued

| Impurity Type | Formul. No. 2 | Formul. No. 3 | Formul. No. 4 | Formul. No. 5 | Formul. No. 6 |
|---|---|---|---|---|---|
| (RT 10.999) | 0.10% | 0.06% | — | 0.04% | 0.04% |
| (RT 12.414) | 0.29% | 0.18% | 0.04% | 0.09% | 0.11% |
| (RT 13.826) | 0.09% | (RT 12.281) | (RT 13.116) | (RT 12.979) | (RT 12.651) |
| (RT 15.169) | 0.19% | (RT 13.694) | 0.06% | (RT 13.514) | (RT 13.273) |
| (RT 16.063) | 0.09% | — | (RT 13.519) | — | — |
| (RT 21.475) | 0.03% | — | — | — | — |
| (RT 33.446) | 0.26% | 0.28% | 0.35% | — | — |
| (RT 34.556) | 0.57% | (RT 34.079) | (RT 33.775) | 0.29% | 0.33% |
| (RT 38.438) | (RT 38.438) | 0.45% | 0.15% | (RT 37.333) | (RT 36.645) |
|  | — | (RT 37.860) | (RT 37.542) | 0.05% | 0.05% |
|  |  | — | 0.04% | (RT 44.110) | (RT 43.147) |
|  | 1.63% | 1.14% | (RT 44.286) | 0.59% | 0.68% |
|  | (RT 46.576) | (RT 45.821) | 0.29% (RT 45.503) | (RT 45.245) | (RT 44.430) |

Figure 3:
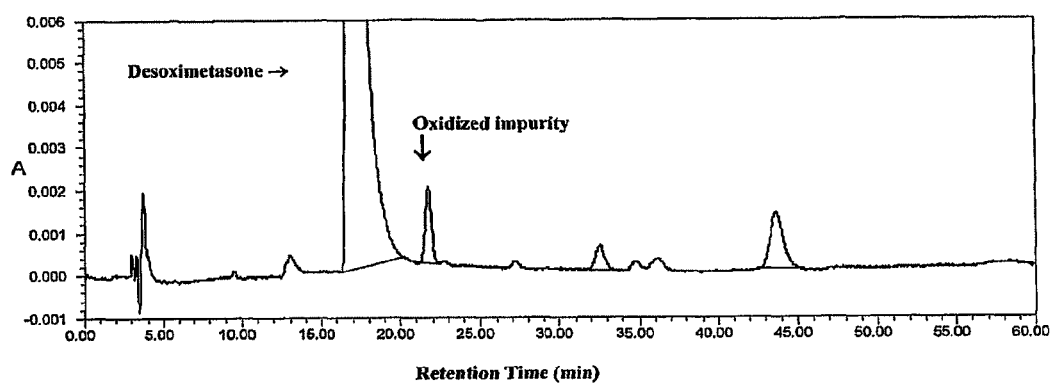

The entire HPLC chromatogram summarizing the impurity profile for formulation no. 5 (containing anti-oxidant of citric acid and tartaric acid) at time zero is shown in FIG. 3.

Figure 4:
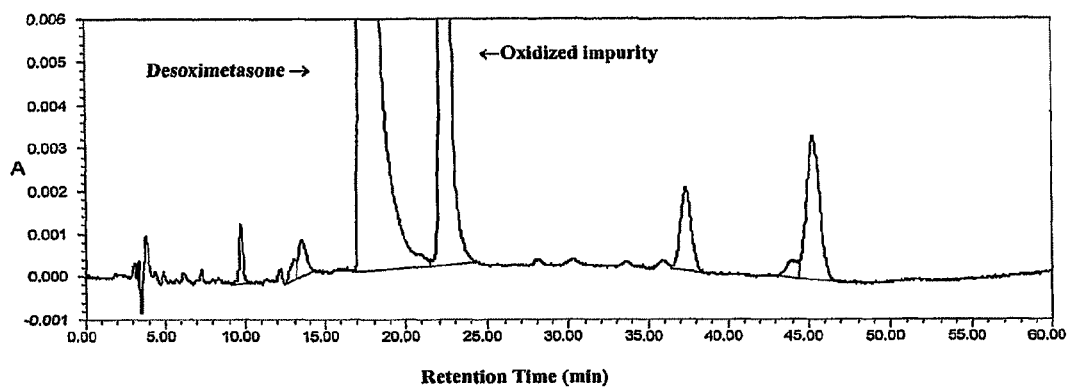

The entire HPLC chromatogram summarizing the impurity profile for formulation no. 5 (containing anti-oxidant of citric acid and tartaric acid) after storage at 50° C. for 4 weeks is shown in FIG. 4.

Example 5

Formulations Nos. 7-10 Containing Desoximetasone and Isopropyl Alcohol and a Mixture of Mineral Oil Light and Oleyl Alcohol Formulation: Formulations nos. 7-10 containing desoximetasone and isopropyl myristate were prepared with specified ingredients as listed in Table 7.

TABLE 7

| Ingredients | Formulation No. 7 | Formulation No. 8 | Formulation No. 9 | Formulation No. 10 |
|---|---|---|---|---|
| Active |  |  |  |  |
| Desoximetasone | 0.25% | 0.25% | 0.25% | 0.25% |
| Penetration Enhancer |  |  |  |  |
| Isopropyl Myristate | 10.0% | 40.0% | 10.0% | 10.0% |
| Solvent |  |  |  |  |
| Isopropyl Alcohol | 25.0% | 20.0% | 30.0% | 40.0% |
| Stabilizing agent |  |  |  |  |
| Oleyl Alcohol | 8.0% | 5.0% | 8.0% | 5.0% |
| Mineral Oil Light | 43.60% | 29.60% | 43.60% | 37.20% |
| Other Excipients |  |  |  |  |
| Menthol | 0.05% | 0.05% | 0.05% | 0.05% |
| Cyclomethicone | 8.0% | 5.0% | 8.0% | 7.50% |

TABLE 7-continued

| Ingredients | Formulation No. 7 | Formulation No. 8 | Formulation No. 9 | Formulation No. 10 |
|---|---|---|---|---|
| Povidone-K90 | 0.10% | 0.10% | 0.10% | — |
| Isopropyl Palmitate | 5.0% | — | — | — |

Preparation: The formulation nos. 7-10 were prepared as follows: desoximetasone (0.25 wt %) was first dissolved in isopropyl alcohol at room temperature (i.e., 25° C.). Isopropyl myristate was added to the mixture followed by oleyl alcohol, cyclomethicone and mineral oil light, menthol and isopropyl palmitate. Where applicable, povidone-K90 (i.e., formulations 8-10) was premixed in isopropyl alcohol. The resulting mixture was further stirred for 15 minutes at room temperature.

Stability Study: We conducted the stability studies of formulation nos. 7-10 by subjection the formulations under the accelerated storage condition (i.e., 40° C. at 75% relative humidity for 12 weeks). Formulation nos. 7-10 containing desoximetasone and isopropyl myristate were placed in a 20-ml glass vials. Content of desoximetasone and impurities were evaluated using HPLC technique. The data is tabulated in Table 8.

TABLE 8

| Content | Time points | Formul. No. 7 | Formul. No. 8 | Formul. No. 9 | Formul. No. 10 |
|---|---|---|---|---|---|
| Desoximetasone (% Time Zero) | 0 week | 100.0% | 100.0% | 100.0% | 100.0% |
|  | 4 weeks | 100.0% | 100.0% | 100.5% | 100.5% |
|  | 8 weeks | 98.48% | 100.49% | 101.03% | 100.5% |
|  | 12 weeks | 100.0% | 100.62% | 102.17% | 100.62% |
| Oxidized Impurity (% Area) | 0 week | 0.05% | 0.05% | 0.10% | 0.07% |
|  | 4 weeks | 0.07% | 0.07% | 0.10% | 0.09% |
|  | 8 weeks | 0.24% | 0.10% | 0.11% | 0.20% |
|  | 12 weeks | 0.49% | 0.39% | 0.17% | 0.26% |

Impurity Profile: Table 9 depicts the impurity profile of the formulation nos. 7-10 after accelerated storage condition (i.e., at 40° C. at 75% humidity for 12 weeks).

The main impurity present in the formulation nos. 7-10 was the oxidized impurity (17-carboxy-9α-fluoro-11β-hydroxy- 16α-methyl-androsta-1,4-diene-3-one). The oxidized impurity has a distinct retention time of about 23.612 to about 30.951, due to the intrinsic variations of the HPLC running conditions. The maximum % area of the oxidized impurity was 0.53 (i.e., formulation no. 7). The minimum % area of the oxidized impurity was 0.17 (i.e., formulation no. 9).

At least one minor impurity was observed in each of the formulation nos. 7-10. This minor impurity for formulation no. 7 has a retention time of about 6.378; while the minor impurity of the formulation nos. 8-10 has a retention time of about 28.063 to about 28.512, due to the intrinsic variations of the HPLC running conditions. Based on the difference in the retention time, the minor impurity present in formulation no. 7 appears to be different from that of formulations 8-10. The identity of the minor impurity is presently unknown. The maximum % area of the minor impurity was 0.13 (i.e., formulation no. 7). The minimum % area of the minor impurity was 0.09 (i.e., formulation nos. 8-10). Based on their retention times, it is believed that they do not overlap with those of: 1) impurity S, and 2) 17-desoxiosido.

TABLE 9

| Impurity Type | Formulation No. 7 | Formulation No. 8 | Formulation No. 9 | Formulation No. 10 |
|---|---|---|---|---|
| Oxidized Impurity | 0.53% (RT 23.612) | 0.39% (RT 30.472) | 0.17% (RT 30.718) | 0.26% (RT 30.951) |
| Unknown Impurity | 0.13% (RT 6.378) | 0.09% (RT 28.063) | 0.09% (RT 28.293) | 0.09% (RT 28.512) |

Figure 5:
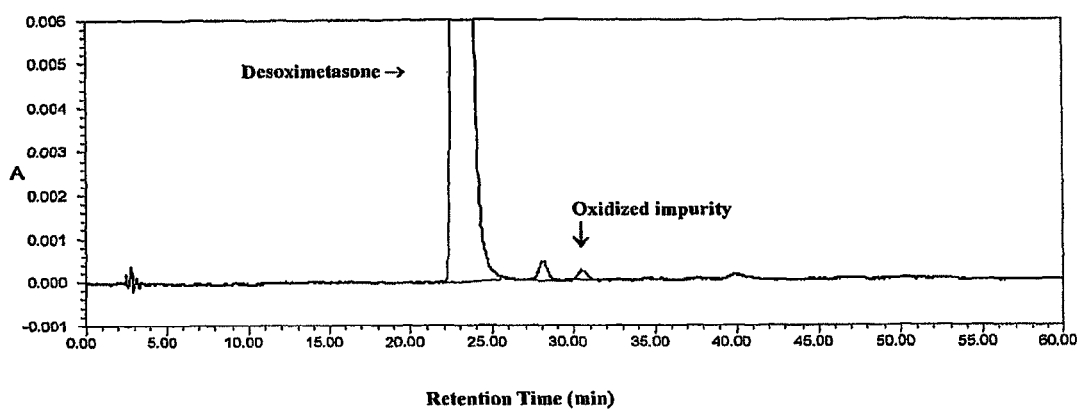

The entire HPLC chromatogram summarizing the impurity profile for formulation no. 7 (containing a stabilizing agent of a mixture of mineral oil and oleyl alcohol) at time zero is shown in FIG. 5.

Figure 6:
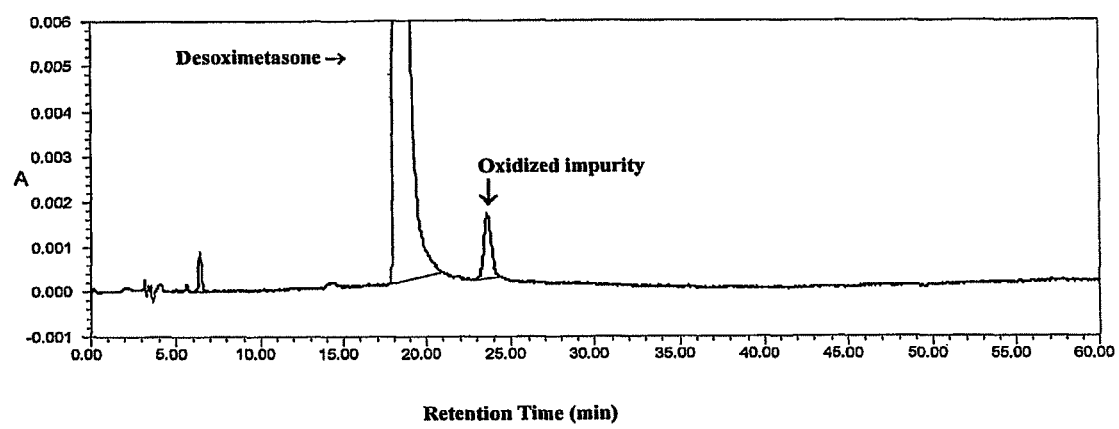

The entire HPLC chromatogram summarizing the impurity profile for formulation no. 7 (containing a stabilizing agent of a mixture of mineral oil and oleyl alcohol) after storage at 40° C./75% relative humidity for 12 weeks is shown in FIG. 6.

Example 6

Formulation No 11 Containing Desoximetasone and Isopropyl Myristate in a Mixture of Mineral Oil and Glyceryl Oleate Formulation: Control formulation no. 11 containing desoximetasone and isopropyl myristate was prepared with specified ingredients as tabulated in Table 10.

TABLE 10

| Ingredients | wt % |
|---|---|
| Active | |
| Desoximetasone | 0.30% |
| Penetration Enhancer | |
| Isopropyl Myristate | 31.35% |
| Solvent | |
| Isopropyl Alcohol | 23.40% |
| Stabilizing agent | |
| Glyceryl Oleate | 0.90% |
| Mineral Oil | 44.0% |
| Other Excipients | |
| Menthol | 0.05% |

Preparation: The formulation no. 11 was prepared as follows: desoximetasone (0.30 wt %) was dissolved in isopropyl alcohol (23.40 wt %) at room temperature (i.e., 25° C.). Isopropyl myristate (31.35 wt %) was added to the mixture followed by glyceryl oleate (0.90 wt %), mineral oil (44.0 wt %) and menthol (0.05 wt %). The resulting mixture was further stirred for 15 minutes at room temperature.

Stability Study: We conducted the stability study for formulation no. 11 by subjecting the formulation under accelerated storage condition (i.e., 40° C. at 75% humidity for 12 weeks). Formulation no. 11 was placed in a 20-ml glass vial and stored at 40° C. at 75% humidity for 12 weeks. Content of desoximetasone and impurities were evaluated using HPLC technique. The data is tabulated in Table 11.

TABLE 11

| Content | 0 Week | 12 Weeks |
|---|---|---|
| Desoximetasone (% Time Zero) | 100.0% | 99.16% |
| Oxidized Impurity (% Area) | 0.05% | 0.07% |

Impurity Profile: Table 12 depicts the impurity profile of the formulation no. 11 after the accelerated storage condition (i.e., 40° C. and 75% humidity for 12 weeks). The main impurity present in formulation no. 11 was the oxidized impurity (17-carboxy-9α-fluoro-11β-hydroxy-16α-methyl-androsta-1,4-diene-3-one). The oxidized impurity has a retention time of about 23.7. The % area of the oxidized impurity was 0.07. There was only one minor impurity present in the formulation no. 11. The total % area of the minor impurity was about 0.11.

TABLE 12

| Impurity Type | RT | Formulation No. 11 |
|---|---|---|
| Oxidized Impurity | 23.7 | 0.07% |
| Unknown | 6.405 | 0.11% |

Figure 7:
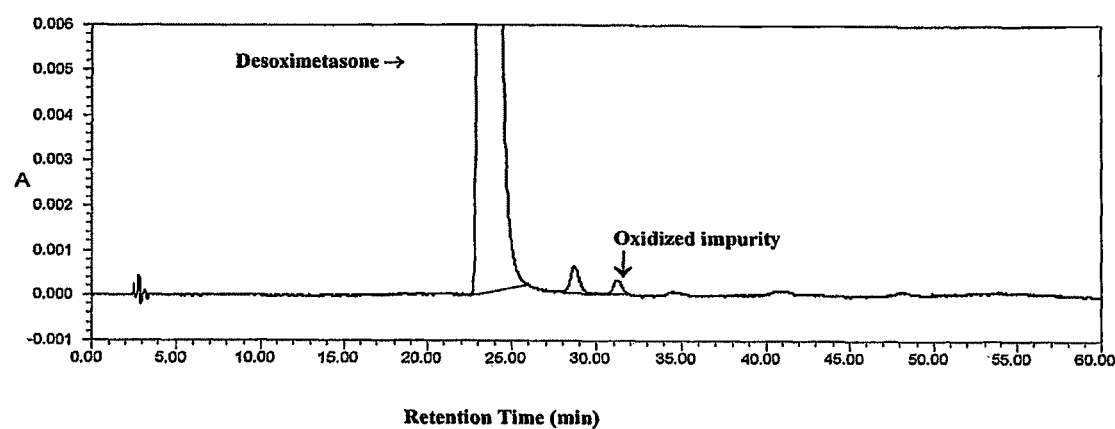

The entire HPLC chromatogram summarizing the impurity profile for formulation no. 11 (containing a stabilizing agent of a mixture of mineral oil and glyceryl oleate) at time zero is shown in FIG. 7.

Figure 8:
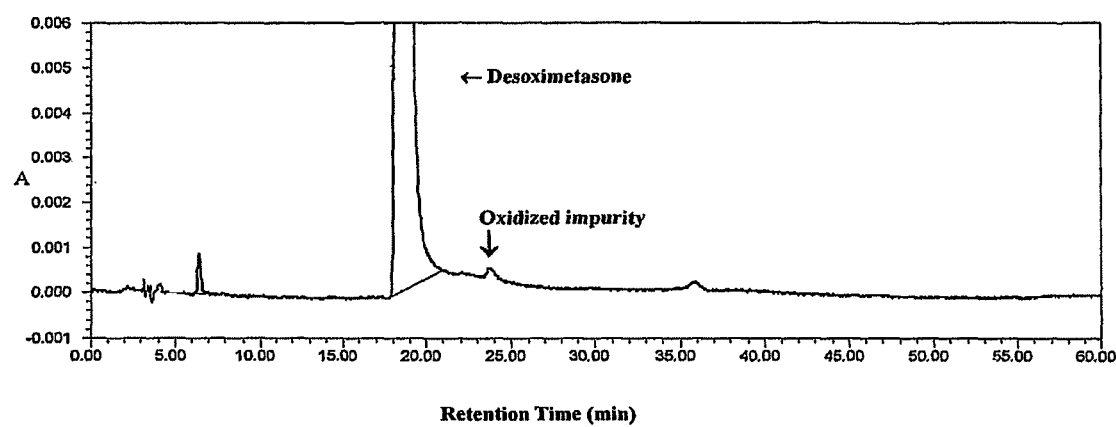

The entire HPLC chromatogram summarizing the impurity profile for formulation no. 11 (containing a stabilizing agent of a mixture of mineral oil and glyceryl oleate) after storage at 40° C./75% relative humidity for 12 weeks is shown in FIG. 8.

Example 9

Formulation No. 12 Containing Desoximetasone and Isopropyl Myristate in Propellant Formulation: Formulation no. 12 containing desoximetasone and isopropyl myristate was prepared with specified ingredients as tabulated in Table 13.

TABLE 13

| Ingredients | wt % |
|---|---|
| Active | |
| Desoximetasone | 0.07% |
| Penetration Enhancer | |
| Isopropyl Myristate | 10.0% |

TABLE 13-continued

| Ingredients | wt % |
| --- | --- |
| Solvent | |
| Purified Water | 0.85% |
| Ethyl Alcohol | 13.70% |
| Surfactant | |
| Sodium Lauryl Sulfate | 0.03% |
| Polysorbate 80 | 0.35% |
| Propellant | |
| 1,1,1,2-Tetrafluoroethane (Dymel 134a/P ®) | 75% |

Preparation: The formulation was prepared as follows: desoximetasone (0.07 wt %) was first dissolved in ethyl alcohol (13.70 wt %) at room temperature (i.e., 25° C.). Isopropyl myristate (10.0 wt %) was added to the mixture followed by purified water (0.85 wt %), sodium lauryl sulfate (0.03 wt %), and polysorbate 80 (0.35 wt %). The resulting mixture was further stirred for 15 minutes at room temperature. The resulting mixture was first introduced into a coated aluminum can equipped with a continuous spray valve. 75 wt % propellant (i.e., 1,1,1,2-Tetrafluoroethane, Dymel 134a/P®) was then introduced into the aluminum can quantity sufficient to make up the total volume to 100 wt %.

Stability Study: We conducted the stability of formulation no. 12 by subjecting the formulation under accelerated storage condition (i.e., 40° C. at 75% humidity for 12 weeks). Formulation no. 12 containing desoximetasone and isopropyl myristate was packaged in 100-ml coated aluminum canisters and stored at 40° C. at 75% humidity for 12 weeks. Content of desoximetasone and impurities were evaluated using HPLC technique. The data is tabulated in Table 14.

TABLE 14

| Content | 0 Week | 12 Weeks |
| --- | --- | --- |
| Desoximetasone (% Time Zero) | 100.0% | 92.0% |
| Oxidized Impurity (% Area) | 0.53% | 0.45% |

Impurity Profile: Table 15 depicts the impurity profile of the formulation no.12 after storage at 40° C. and 75% humidity for 12 weeks. The main impurity present in formulation no. 12 was the oxidized impurity (17-carboxy-9α-fluoro-11β-hydroxy-16α-methyl-androsta-1,4-diene-3-one). The oxidized impurity has a retention time (RT) of about 22.110. The % area of the oxidized impurity was 0.45. No minor impurity was found to be present in formulation no. 12, either at time zero

Example 9

Formulation No. 12 Containing Desoximetasone and Isopropyl Myristate in Propellant Formulation: Formulation no, 12 containing desoximetasone and isopropyl myristate was prepared with specified ingredients as tabulated in Table 13.

TABLE 13

| Ingredients | wt % |
| --- | --- |
| Active | |
| Desoximetasone | 0.07% |
| Penetration Enhancer | |
| Isopropyl Myristate | 10.0% |
| Solvent | |
| Purified Water | 0.85% |
| Ethyl Alcohol | 13.70% |
| Surfactant | |
| Sodium Lauryl Sulfate | 0.03% |
| Polysorbate 80 | 0.35% |
| Propellant | |
| 1,1,1,2-Tetrafluoroethane (Dymel 134a/P ®) | 75% |

Preparation: The formulation was prepared as follows: desoximetasone (0.07 wt %) was first dissolved in ethyl alcohol (13.70 wt %) at room temperature (i.e., 25° C.). Isopropyl myristate (10.0 wt %) was added to the mixture followed by purified water (0.85 wt %), sodium lauryl sulfate (0.03 wt %), and polysorbate 80 (0.35 wt %). The resulting mixture was further stirred for 15 minutes at room temperature. The resulting mixture was first introduced into a coated aluminum can equipped with a continuous spray valve. 75 wt % propellant (i.e., 1,1,1,2-Tetrafluoroethane, Dymel 134a/P®) was then introduced into the aluminum can quantity sufficient to make up the total volume to 100 wt %.

Stability Study: We conducted the stability of formulation no. 12 by subjecting the formulation under accelerated storage condition (i.e., 40° C. at 75% humidity for 12 weeks). Formulation no. 12 containing desoximetasone and isopropyl myristate was packaged in 100-ml coated aluminum canisters and stored at 40° C. at 75% humidity for 12 weeks. Content of desoximetasone and impurities were evaluated using HPLC technique. The data is tabulated in Table 14.

TABLE 14

| Content | 0 Week | 12 Weeks |
| --- | --- | --- |
| Desoximetasone (% Time Zero) | 100.0% | 92.0% |
| Oxidized Impurity (% Area) | 0.53% | 0.45% |

Impurity Profile: Table 15 depicts the impurity profile of the formulation no.12 after storage at 40° C. and 75% humidity for 12 weeks. The main impurity present in formulation no. 12 was the oxidized impurity (17-carboxy-9α-fluoro-11β-hydroxy-16α-methyl-androsta-1,4-diene-3-one). The oxidized impurity has a retention time (RT) of about 22.110. The % area of the oxidized impurity was 0.45. No minor impurity was found to be present in formulation no. 12, either at time zero or after storage at 40° C. and 75% humidity for 12 weeks. These data support that the stabilizing agent is extremely effective in inhibiting the production of both oxidized impurity as well as minor impurities.

TABLE 15

| Impurity Name | RT | Formulation No. 12 |
|---|---|---|
| Oxidized | 22.110 | 0.45% |
| Unknown Impurity | — | — |

Figure 9:
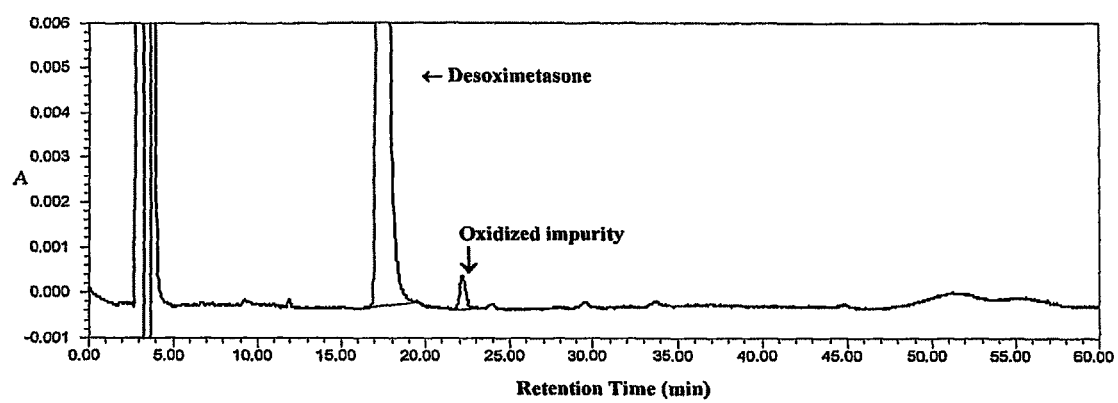

The entire HPLC chromatogram summarizing the impurity profile for formulation no. 12 (containing a stabilizing agent of a propellant) at time zero is shown in FIG. 9.

Figure 10:
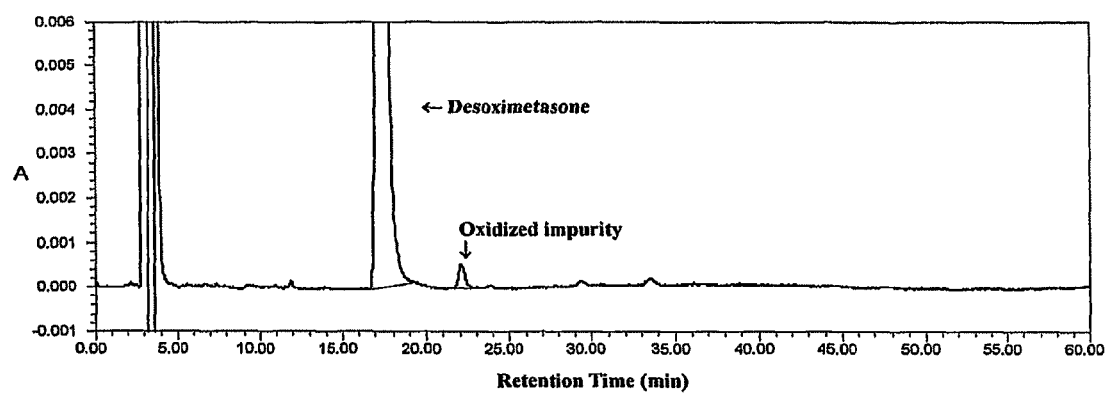

The entire HPLC chromatogram summarizing the impurity profile for formulation no. 11 (containing a stabilizing agent of a propellant) after storage at 40° C./75% relative humidity for 12 weeks is shown in FIG. 10.

Those skilled in the art will recognize, or be able to ascertain using no more than routine experimentation, many equivalents of the specific embodiments of the invention described herein. The disclosures of the cited publications are incorporated herein in their entireties by reference. It is to be understood, however, that the scope of the present invention is not to be limited to the specific embodiments described above. The invention may be practiced other than as particularly described and still be within the scope of the accompanying claims.

What is claimed is:

1. A liquid formulation comprising:
    a) about 0.01 wt % to about 2.5 wt % desoximetasone;
    b) about 10 wt % to about 70 wt % isopropyl myristate;
    c) about 20 wt % to about 70 wt % $C_2$-$C_4$ alcohol; and
    d) a stabilizing agent comprising a mixture of
        (1) an oleaginous vehicle selected from the group consisting of mineral oil and light mineral oil and
        (2) a skin conditioning agent selected from one or more of the group consisting of
            (i) a $C_{15}$-$C_{25}$ fatty alcohol present in the amount of about 0.5 wt % to about 10 wt %, and
            (ii) an ester of glycerin and a $C_{15}$-$C_{25}$ fatty acid present in the amount of about 0.5 wt % to about 10 wt %.

2. The liquid formulation of claim 1, wherein the desoximetasone is present in an amount of about 0.1 wt % to about 1 wt %.

3. The liquid formulation of claim 1, wherein the desoximetasone is present in an amount of about 0.25 wt %.

4. The liquid formulation of claim 1, wherein the isopropyl myristate is present in an amount of about 25 wt % to about 55 wt %.

5. The liquid formulation of claim 1, wherein the isopropyl myristate is present in an amount of about 40 wt %.

6. The liquid formulation of claim 1, wherein the $C_2$-$C_4$ alcohol is ethyl alcohol.

7. The liquid formulation of claim 1, wherein the $C_2$-$C_4$ alcohol is isopropanol.

8. The liquid formulation of claim 1, wherein the $C_2$-$C_4$ alcohol is present in an amount of about 30 wt % to about 60 wt %.

9. The liquid formulation of claim 1, wherein the $C_2$-$C_4$ alcohol is present in an amount of about 40 wt %.

10. The liquid formulation of claim 1, wherein the oleaginous vehicle is mineral oil.

11. The liquid formulation of claim 1, wherein the skin conditioning agent comprises a ester of a glycerin and a $C_{15}$-$C_{25}$ fatty acid.

12. The liquid formulation of claim 11, wherein the ester is glyceryl oleate.

13. The liquid formulation of claim 11, wherein the ester is present in the amount of about 1 wt % to about 8 wt %.

14. The liquid formulation of claim 11, wherein the ester is present in the amount of about 0.9 wt %.

15. The liquid formulation of claim 1, wherein the skin conditioning agent comprises a $C_{15}$-$C_{25}$ fatty alcohol selected from the group consisting of lauryl alcohol, myristyl alcohol, palmityl alcohol, stearyl alcohol, linoleyl alcohol, and oleyl alcohol.

16. The liquid formulation of claim 15, wherein the $C_{15}$-$C_{25}$ fatty alcohol is present in the amount of about 1 wt % to about 8 wt %.

17. The liquid formulation of claim 15, wherein the $C_{15}$-$C_{25}$ fatty alcohol is present in the amount of about 5 wt %.

18. The liquid formulation of claim 1, wherein the propellant is selected from the group consisting of 1,1,1,2-tetrafluoroethane, 1,1,1,2,3,3,3-heptafluoropropane, butane, isobutane, propane, and dimethyl ether.

19. The liquid formulation of claim 1, wherein the propellant is present in an amount of about 20 wt % to about 95 wt %.

20. The liquid formulation of claim 1, wherein the propellant is present in an amount of about 20 wt % to about 75 wt %.

21. The liquid formulation of claim 1, further comprising a surfactant selected from the group consisting of sodium lauryl sulfate, and polysorbate 80.

22. The liquid formulation of claim 21, wherein the surfactant is present in the amount of about 0.5 wt % to about 5 wt %.

23. The liquid formulation of claim 1, wherein the liquid formulation is stable after storage at 50° C. for 4 weeks.

24. A dosage form comprising the liquid formulation of claim 1, and further comprising a pump delivery system.

25. A dosage form comprising the liquid formulation of claim 1, and further comprising an aerosolized delivery system.

26. The dosage form of claim 25, wherein the aerosolized delivery system contains a can equipped with a continuous valve.

27. The dosage form of claim 25, wherein the aerosolized delivery system contains a can equipped with a metered-dosed valve.

28. The liquid formulation of claim 1, wherein the liquid formulation is a foam.

29. The dosage form of claim 27, wherein the foam is a quick-break foam.

30. A method of treating a corticosteroid responsive dermatosis in a mammal comprising the step of topical administering the aerosolized formulation of claim 1.

31. The method of claim 30, wherein the corticosteroid responsive dermatosis is selected from the group consisting of plaque psoriasis, and atopic dermatitis.

32. A process for preparing a liquid formulation comprising:
    a) mixing desoximetasone in a $C_2$-$C_4$ alcohol to from a mixture;
    b) adding isopropyl myristate in the mixture; and
    c) adding a stabilizing agent comprising a mixture of
        (1) an oleaginous vehicle selected from the group consisting of mineral oil and light mineral oil and
        (2) a skin conditioning agent selected from one or more of the group consisting of
            (i) a $C_{15}$-$C_{25}$ fatty alcohol present in the amount of about 0.5 wt % to about 10 wt %, and
            (ii) an ester of glycerin and a $C_{15}$-$C_{25}$ fatty acid present in the amount of about 0.5 wt % to about 10 wt %.

33. A process for preparing an aerosolized formulation of desoximetasone comprising the step of filling an aerosol formulation into a container equipped with a continuous valve, wherein said aerosol formulation contains:
- a) about 0.01 wt % to about 2.5 wt % desoximetasone;
- b) about 10 wt % to about 70 wt % isopropyl myristate;
- c) about 20 wt % to about 70 wt % $C_2$-$C_4$ alcohol; and
- d) a stabilizing agent comprising a mixture of
   - (1) an oleagenous vehicle selected from the group consisting of mineral oil and light mineral oil and
   - (2) a skin conditioning agent selected from one or more of the group consisting of
      - (i) a $C_{15}$-$C_{25}$ fatty alcohol present in the amount of about 0.5 wt % to about 10 wt %, and
      - (ii) an ester of glycerin and a $C_{15}$-$C_{25}$ fatty acid present in the amount of about 0.5 wt % to about 10 wt %.

* * * * *

UNITED STATES PATENT AND TRADEMARK OFFICE
CERTIFICATE OF CORRECTION

| | | |
|---|---|---|
| PATENT NO. | : 8,715,624 B2 | Page 1 of 1 |
| APPLICATION NO. | : 13/605622 | |
| DATED | : May 6, 2014 | |
| INVENTOR(S) | : Rao et al. | |

It is certified that error appears in the above-identified patent and that said Letters Patent is hereby corrected as shown below:

On the Title Page, Item (54) and in the Specification, Col. 1, Line 1, Title should read as follows:

-- STABLE LIQUID ~~DESOXIMETHASONE~~ DESOXIMETASONE COMPOSITIONS WITH REDUCED OXIDIZED IMPURITY --.

Signed and Sealed this
Thirtieth Day of September, 2014

Michelle K. Lee
*Deputy Director of the United States Patent and Trademark Office*